United States Patent [19]

Skov et al.

[11] Patent Number: 5,026,694
[45] Date of Patent: Jun. 25, 1991

[54] PLATINUM COMPLEXES WITH ONE RADIOSENSITIZING LIGAND

[75] Inventors: Kirsten A. Skov, Vancouver, Canada; Nicholas P. Farrell, Winooski, both of Vt.; David J. Chaplin, Richmond, Canada

[73] Assignee: The British Columbia Cancer Foundation, Vancouver, Canada

[21] Appl. No.: 374,356

[22] Filed: Jun. 30, 1989

Related U.S. Application Data

[63] Continuation-in-part of Ser. No. 37,498, Apr. 13, 1987, Pat. No. 4,921,963.

[51] Int. Cl.$^5$ ........................................... A61K 31/555
[52] U.S. Cl. .................................................. 514/184
[58] Field of Search ....................................... 514/184

[56] References Cited

U.S. PATENT DOCUMENTS

| | | | |
|---|---|---|---|
| 3,794,648 | 2/1974 | Hammond et al. | 546/2 |
| 3,879,416 | 4/1975 | Kraus et al. | 548/359 |
| 4,511,715 | 4/1985 | Palensky et al. | 544/225 |
| 4,661,516 | 4/1987 | Brown et al. | 514/492 |

FOREIGN PATENT DOCUMENTS

| | | |
|---|---|---|
| 2093451 | 2/1982 | United Kingdom . |
| 2122194 | 6/1983 | United Kingdom . |

OTHER PUBLICATIONS

Rosenberg (1980) "Cisplatin: Its History and Possible Mechanisms of Action," (Academic Press) pp. 9-20.
Roberts (1981) "The Mechanism of Action of Anti-Tumour Platinum Coordination Compounds," (Elsevier) pp. 273-332.
Rosenberg (1978), interdisciplinary Science Reviews, 3(2):4-29.
Doadrio, et al. (1978), Inorganic Perspectives in Biology and Medicine, 1:223-231.
Farrell, et al. (1982), Radiation Research, 91:378 (abstract).
Skov, et al., Abstracts of Papers for the Thirty-Second Annual Meeting of the Radiation Research Society, Orlando, Florida, Mar. 25-29, 1984.
Chan, et al., Abstracts of the Papers for the Thirty—Third Annual Meeting of the Radiation Research Society, Los Angeles, CA, May 5-9, 1985.
Skov, et al., Abstracts of Papers for the Thirty-Third Annual Meeting of the Radiation Research Society, Los Angeles, CA, May 5-9, 1985.
Adomat, et al., Abstracts of Papers for the Thirty-Fourth Annual Meeting of the Radiation Research Society, Las Vegas, Nevada, Apr. 12-17, 1986.
Chan, et al., (1986), Int. J. Radiation Oncology Biol. Phys., 12:1059-1062.
Chan, et al., (1986) Chem. Biol. Interaction, 59:247-254.
Farrell, et al., (1984) Inorganica Chemica Acts, 92:61-66.
Bales, et al., (1982), Br. J. Cancer, 46:701-705.
Chibber, et al., (1984), Radiation Oncology Biol. Phys., 10:1213-1215.
Bocian, et al., (1983), Br. J. Cancer, 48:803-807.
Teicher, et al., (1985), Int. J. Radiation Oncology Biol. Phys., 11:937-941.
Skov, et al., (1987) Chem. Biol. Interact., 62:117-129.

Primary Examiner—Stanley J. Friedman
Assistant Examiner—Gary E. Hollinden
Attorney, Agent, or Firm—Irell & Manella

[57] ABSTRACT

Methods to inhibit tumor growth and to radiosensitize hypoxic cells and pharmaceutical compositions therefor are disclosed. These methods and compositions use compounds of the formula $$PtX_n(NR_2H)(L) \qquad (1)$$

wherein n is 1 or 2, and
wherein when n is 2, X is a monovalent biologically acceptable anion, and when n is 1, X is a divalent biologically acceptable anion;
each R is independently H or alkyl, or both Rs together are a piperidino or morpholino residue; and
L is a radiosensitizing ligand selected from a mononitro-substituted imidazole, a mononitro-substituted pyrazole, a mononitro-substituted thiazole and a mononitro-substituted isothiazole.

30 Claims, 8 Drawing Sheets

PLATINUM COMPLEXES WITH ONE RADIOSENSITIZING LIGAND

CROSS-REFERENCE TO RELATED APPLICATION

This application is a continuation-in-part of U.S. Ser. No. 037,498, filed 13 April 1987, now U.S. Pat. No. 4,921,963.

TECHNICAL FIELD

The invention relates to the design of metallo-organic complexes suitable for tumor therapy. In particular, it relates to platinum complexes containing only one radiosensitizing ligand which are effective in sensitizing hypoxic cells to radiation, and are also toxic to tumor cells in vivo sensitive to such treatment.

BACKGROUND ART

Apart from surgery, there have been only two general approaches to tumor therapy which have been major viable alternatives in the past two decades. Although these approaches are far from perfect, sufficiently acceptable results have been obtained that, despite considerable problems with side effects and unpredictability of efficacy, these methods are, in fact, utilized in the treatment of patients.

These two approaches are, of course, chemotherapy and radiation treatment. In chemotherapy, the subject is treated with a suitable pharmaceutical substance in protocols which generally do not differ markedly from administration of other drugs. The tumor selectivity of the drug is an inherent function of its chemical nature, and most such drugs are chosen because they selectively interfere with rapidly growing cells. The radiation-centered approach can also be aided by administration of chemical substances to enhance the effectiveness of the treatment, i.e., radiosensitizers. This is particularly important for treatment of solid tumors using radiation, since the lethal power of radiation is diminished by the hypoxic nature of most tumors. Hypoxia, in general, renders cell masses relatively resistant to radiation, and thus a mechanism for overcoming this resistance may be supplied in the form of radiosensitizers which, possibly, substitute for oxygen in sensitizing the cells to the effects of the radiation.

The number of compounds which have been used as chemotherapeutic agents is large, and many of the compounds utilized are unrelated to those of the present invention. Those most closely related to the invention herein include the complexes of platinum II of square planar configuration, and, in particular, the cis-isomeric forms. As early as 1969, cis-platin (cis[PtCl$_2$(NH$_3$)$_2$]) was shown to have antineoplastic activity. This compound is now widely used in clinics, with second generation compounds in clinical trials since 1979. It has also been possible to substitute other metals such as ruthenium and palladium for platinum as the center ion of the complex, and alternative ligands to the chloride and amino groups, such as DMSO, ethylenediamine, and so forth, have been studied (Farrell, N. P., et al, *Biochem Pharmacol* (1984) 33:961-973). The conventional wisdom as stated in the Farrell paper and elsewhere (Rosenberg, B., in "Cisplatin: Current Status and New Developments" (1980) Prestayko, A. W., et al, eds, Academic Press, pp. 9 et seq.; Rosenberg, B., *Interdisciplinary Science Reviews* (1978) 3:1-29; Roberts, J. J., in *Metal Ions in Genetic Information Transfer* (1981) Elsevier, pp. 273 et seq.), is that the cis-isomer is required for antitumor activity.

With regard to radiosensitizing compounds, a number of mono-nitroimidazole and mono-nitrothiazole derivatives have been shown to exhibit this activity. For example, metronidazole (METRO), misonidazole (MISO), and certain proprietary compounds such as SR-2508 (etanidazole) have been shown to have beneficial effects in sensitizing cells to radiation treatment in clinical trials (Overgaard, J., et al, in *Proc 3rd Int Meeting on Prog Radio Onc*, Raven Press, New York (1986)). METRO and MISO have been studied extensively, and MISO is commonly used as a standard in in vivo and in vitro tests for radiosensitizing activity (Asquith et al, *Radiation Res* (1974) 60:108-118; Hull et al, *Brit J Cancer* (1978) 37:567-569; Brown et al, *Radiation Res* (1980) 82:171-190; U.S. Pat. No. 4,371-540).

Because these compounds are toxic in the amounts needed to be administered in order for the effect to be exhibited, it has been attempted to utilize metals known to bind to DNA to carry the organic radiosensitizer to the target. Exemplary reports of this approach include Farrell, N. P., et al, *Radiation Research* (1982) 91:378-379; Bales, J. R., et al, *Brit J Cancer* (1982) 46:701-705; Bales, J. R., et al, *J Chem Soc Chem Comm* (1983) 432-433; Chibber, R., et al, *Int J Radiation Oncol Biol Phys* (1984) 1213-1215; Teicher, D. A., et al, ibid (1984) 11:937-941; Skov, K. A., et al, *Proc 7th Intl Cong Radiation Research* (Amsterdam); Broerse, J. J., et al, eds., Abstract B6-29, Martinus Nijhoff (1983), The Hague; Farrell, N. P., et al, *Inorg Chim Acta* (1984) 92:61-66; Chan, P. K. L., *Int J Radiation Oncol Biol Phys* (1986) 12:1059-1062. All of these reports are directed to radiosensitization studies using metal complexes with known radiosensitizers in complexes which are bivalent for the radiosensitizing material. In addition, the sensitization of hypoxic cells to radiation as effected by complexes of platinum and related metals with no sensitizing ligand (e.g. Douple, E. B., et al, *Brit J Cancer* Suppl III (1978) 37:98-102) is being exploited clinically. Nias, A. H. W., *Int J Radiation Biol* (1985) 48:297-314, has presented a review of the various approaches to this problem.

The Teicher et al article is particularly relevant because it discloses, among several platinum-containing complexes bisubstituted with radiosensitizers, the mono-substituted platinum complex of 1,2-diamino-4-nitrobenzene as a bidentate complex. This compound, designated "Plato" by Teicher, showed a high capacity for killing of hypoxic cells and less toxicity toward oxygenated cells. In addition, British patent application 2,093,451A and 2,122,194A disclose metal complexes of nitro-substituted pyrazoles, nitrazoles, imidazoles, and isothiazoles. These compounds are claimed to be useful in the therapy of cancer and to have antibacterial activity.

The history of cancer treatment using either direct chemotherapy or radiation with sensitization by compounds of appropriate electron affinity, such as misonidazole, shows that there is a high variability between individuals and individual tumors with regard to the sensitivity to particular reagents. That is, it seems to be unpredictable in advance what protocols, what sensitizing agents, and what chemotherapeutic agents, if any, will work in an individual instance. Some tumors appear to be easily permanently destroyed by radiation, while other are resistant. Certain tumors are responsive to, for example, cytoxan or prednisone, while others are not. A similar situation is expected to exist with regard to the heavy metal complexes containing organic ligands which are toxic to tumors or are radiosensitizers. For example, cisplatin has proven useful in the treatment of testicular cancer, but less so in treatment of cancers at other sites.

Therefore, it becomes crucial to have available a large repertoire of possibilities so that the probability that a given subject will respond to at least one or two members of the repertoire will be maximized. The present invention makes a contribution to this repertoire by adding a series of compounds which have been heretofore unavailable, and which have been shown to be effective in radiosensitizing hypoxic cells, including tumors, in model systems, as well as to have tumor toxicity in vivo even in the absence of radiation.

DISCLOSURE OF THE INVENTION

The invention compounds are square planar complexes of platinum II, and contain one radiosensitizing ligand and one or two amine or ammine ligands. These compounds are superior to the platinum complexes of the prior art, which bear two radiosensitizing ligands, in their ability to bind DNA and to sensitize hypoxic cells to radiation. In addition, they are directly toxic to tumor cells in vitro and to tumors in animals. The in vivo toxicity of the invention compounds is enhanced by treatment with the vasoactive antihypertensive agent hydralazine.

Therefore, in one aspect, the invention relates to compounds of the formula:

$$[PtX_2(NR_2H)L] \qquad (1)$$

or $$[PtX(NR_2H)_2L]^+Y^- \qquad (2)$$

wherein

X is a monovalent biologically and, in formula (1), X can also represent each "half" of a divalent biologically acceptable anion;

$Y^-$ is a physiologically acceptable anion;

each R is independently H or alkyl, or both Rs together are a piperidino or morpholino residue; and L is a radiosensitizing ligand which is a mononitrosubstituted aromatic moiety containing at least one heterocyclic N and/or substituent amine. Typically, the moiety represented by L is selected from a mononitro-substituted imidazole, a mononitro-substituted pyrazole, a mononitro-substituted thiazole, a mononitro-substituted isothiazole, and a mononitro-substituted quinoline. Other fused ring systems, such as acridine and terpyridine are also included. These heterocycles may additionally be substituted by a substituent $R^1$ which is selected from alkyl optionally containing an amino substituent, $OR^3$, and $N(R^3)_2$, wherein $R^3$ is H or lower alkyl. In addition, if the heterocycle is quinoline, pyrazole or imidazole, a ring nitrogen may be substituted by $R^2$, which is alkyl of 1-8 carbons substituted by one or more $-OR^3$ and wherein one or two methylenes may be replaced by oxygen.

The radiosensitizing ligands are coordinated to the platinum either through a ring nitrogen, or, if the heterocyclic ring is substituted with an amine or aminoalkyl, through either a ring nitrogen or the amine substituent of the ring or alkyl chain.

In other aspects, the invention is directed to pharmaceutical compositions containing effective amounts of the compounds of formulas 1 or 2, and to methods of treating animal subjects including using the compounds of these formulas Subjects can be treated using the compounds of the invention or their pharmaceutical compositions directly in chemotherapeutic regimes, optionally including in these regimes a vasoactive agent, or the compounds may be administered to sensitize tumor cells to treatment by radiation.

In addition, the complexes of the invention may be labeled and used for imaging.

MODES OF CARRYING OUT THE INVENTION

Preferred Embodiments

The compounds of the invention are square planar complexes of platinum II which comprise a single radiosensitizing ligand and one or two ammine or amine substituents. Accordingly, the compounds of the invention may be prepared in either the cis or trans form. The compounds of formula (1) thus include both of the formulas:

$$\begin{array}{cc} \begin{array}{c} L\text{———}X \\ \diagup \text{ Pt } \diagup \\ R_2HN\text{———}X \end{array} & \text{and} & \begin{array}{c} L\text{———}X \\ \diagup \text{ Pt } \diagup \\ X\text{———}NR_2H \end{array} \end{array} \qquad (1)$$

cis     trans

The compounds of formula (2) can be represented by $$\begin{array}{cc} \begin{array}{c} X\text{———}NHR_2 \\ \diagup \text{ Pt } \diagup \\ L\text{———}NHR_2 \end{array} & \text{and} & \begin{array}{c} X\text{———}NHR_2 \\ \diagup \text{ Pt } \diagup \\ R_2HN\text{———}L \end{array} \end{array} \qquad (2)$$

cis     trans

Both the cis and trans forms are useful in the methods of the invention; however, surprisingly, the trans configuration appears to be somewhat more effective. The compounds of the invention can thus be used as isolated isomers or as mixtures of both forms. Procedures for converting the cis to trans form have been published with regard to analogous complexes containing two radiosensitizing ligands (Bales, J. R., et al, *J. Chem Soc Chem Com* (1983) 432–433) and it has been found that these methods are applicable to the complexes containing only one such ligand.

The radiosensitizing ligand is a mono-nitroaromatic moiety. It can be a single 5- or 6-membered ring, or a fused ring system, including pyrrole, aminophenyl, aminonaphthyl, pyridyl, quinoline, or aminothiophene There must be present, of course, at least one of a heterocyclic ring nitrogen or an amino substituent to effect coordination binding of the ligand to the Pt. In the preferred compounds of the invention, this ligand is selected from mononitro-substituted imidazoles, pyrazoles, thiazoles, isothiazoles, and quinolines, and is coordinated to the platinum through a ring nitrogen as in the formulas below, or through an amino group represented by or included in $R^1$, if present. If said amino group is available, complexes wherein coordination is through this group, and complexes wherein coordination is through the ring nitrogen, are both included in the scope of the invention.

Thus, in preferred embodiments, the invention is directed to compounds of formula 1 wherein L is one of the following:

wherein $R^1$ is alkyl optionally containing an amino substituent, $OR^3$, or $N(R^3)_2$, wherein $R^3$ is H or lower alkyl;

$R^2$ is alkyl of 1-8 carbons substituted by one or more $-OR^3$ and wherein one or two methylenes may be replaced by oxygen;

each m independently is 0 or 1.

The single nitro group may be present at positions 2, 4 or 5, for thiazole or imidazole, at positions 3, 4, or 5 for isothiazole or pyrazole, or at any of the ring carbons of quinoline, and the $R^1$ substituent, if present, occupies an alternative site. The nitro group is a prerequisite for activity, as it supplies the electron affinity to the ligand. The $R^1$ substituent is not necessary for activity; hence, the relevant m can be 0.

As used herein, "lower alkyl" refers to a saturated, straight or branched chain hydrocarbyl substituent of 1-4 carbon atoms, for example, methyl, ethyl, n-propyl, i-propyl, n-butyl, sec-butyl, i-butyl, and t-butyl.

"Alkyl" refers to straight, branched chain, or cyclic saturated hydrocarbyl substituents of 1-8 carbons, such as methyl, i-propyl, n-pentyl, i-pentyl, n-octyl, i-octyl, and 3-methylheptyl and cyclohexyl.

Thus, $R^1$ may be methyl, ethyl, n-heptyl, i-octyl, amino, methylamino, dimethylamino, hydroxy, methoxy, ethoxy, and the like. For embodiments which offer the possibility of coordination of L to the metal through a side chain amino, suitable embodiments for $R^1$ include 2-aminoethyl, 4-amino-n-butyl, 3-aminocyclohexyl, 3-amino-n-pentyl, and the like.

With respect to $R^2$, substitution by one or more hydroxyl or lower alkoxy groups on the alkyl group represented by $R^2$ or replacement of one or more methylenes by oxygen is required to enhance the solubility of the compounds. Convenient embodiments of $R^2$ include $CH_2CH(OH)CH_2OCH_3$ and $CH_2CH_2OH$; other preferred embodiments include $-CH_2OCH_2CHOH$.

Particularly preferred compounds of the invention are those wherein L is selected from misonidazole(MISO), which is 1-(2-nitro-1-imidazolyl)-3-methoxypropanol and metronidazole (METRO), which is 1,2-hydroxyethyl-2-methyl-5-nitroimidazole. Also preferred are compounds wherein L is etanidazole (E), 2-amino-5-nitrothiazole (ANT), 4-nitroimidazole (4NI), 5-nitro-imidazole (5NI), 6-nitroquinoline (6NQ) or 5-nitroquinoline (5NQ). These embodiments of L are convenient because they are widely used in the art and are readily available.

Because 4NI and 5NI are tautomeric, when they are not complexed, they do not exist independently. When complexed with Pt, the tautomeric forms are stabilized and can be separated. (Skov, K. et al, Int J Radiat Oncol Biol (1988) in press.)

More particularly preferred are compounds wherein both Rs are H, X is Cl, and L is one of these embodiments—i.e., $[PtCl_2(NH_3)L]$ or $[PtCl(NH_3)_2L]$ as mono-E, mono-MISO, mono-METRO, mono-ANT, mono-4NI, mono-5NI, mono-5NQ or mono-6NQ or their corresponding $di(NH_3)$ forms.

The amine or ammine substituent(s) of the complexes of the invention is preferably $NH_3$. Also included, however, within the scope of the invention are complexes having substituents which are alkyl or dialkylamines, including cyclic alkylamines, such as cyclohexylamine, or embodiments wherein both Rs together form a part of the ring, such as piperidine or morpholino. The amine substituent or substituents are, however, not radiosensitizers, and sufficiently neutral to avoid interference in the ability of the complexes to bind DNA. Indeed it may be that the one or two am(m)ine substituent(s) are a positive factor in DNA binding.

The "biologically acceptable anion" represented by X and $Y^-$, can be any convenient organic or inorganic anion which is a suitable leaving group in vivo. This group is believed to affect the pharmacokinetics of the compounds, and the compound required for binding may be the aquo species. Suitable monovalent anions are, for example, chloride, bromide, nitrate, pyruvate, and acetate. Suitable bivalent anions, which can be present in Formula (1), include bifunctional organic moieties such as malonate or 2-ethyl malonate, oxalate, phthalate or substituted phthalates, and 1,1-cyclobutane dicarboxylate. The sulfate ion can also be used in conjunction with a neutral ligand such as water.

Representative compounds of the invention include the cis and trans forms, and mixtures thereof, of:
$PtCl_2$(ammine)(2-amino-5-nitrothiazole)
$PtCl_2$(ammine)(4-nitrothiazole)
$PtCl_2$(ammine)(5-i-butyl-2-nitrothiazole)
$PtCl_2$(ammine)(2-ethoxy-4-nitrothiazole)
$PtCl_2$(ammine)(2-ethoxy-5-nitrothiazole)
$PtCl_2$(ammine)(4-dimethylamino-2-nitrothiazole)
$PtCl_2$(ammine)(2-t-butoxy-5-nitrothiazole)
$PtCl_2$(ammine)(5-(4-ethylhexyl)-2-nitrothiazole)
$PtCl_2$(ammine)(4-ethylamino-5-nitrothiazole)
$PtCl_2$(ammine)(4-(4-amino-n-butyl)-5-nitrothiazole)
$PtCl_2$(ammine)(2-(6-amino-n-hexyl)-5-nitrothiazole)
$PtCl_2$(dimethylamino)(2-amino-5-nitrothiazole)
$PtCl_2$(dimethylamino)(4-nitrothiazole)

PtCl$_2$(dimethylamino)(5-i-butyl-2-nitrothiazole)
PtCl$_2$(dimethylamino)(2-ethoxy-4-nitrothiazole)
PtCl$_2$(dimethylamino)(2-ethoxy-5-nitrothiazole)
PtCl$_2$(dimethylamino)(4-dimethylamino-2-nitrothiazole)
PtCl$_2$(dimethylamino)(2-t-butoxy-5-nitrothiazole)
PtCl$_2$(dimethylamino)(5-(4-ethylhexyl)-2-nitrothiazole)
PtCl$_2$(dimethylamino)(4-ethylamino-5-nitrothiazole)
PtCl$_2$(dimethylamino)(4-(4-amino-n-butyl)-5-nitrothiazole)
PtCl$_2$(dimethylamino)(2-(6-amino-n-hexyl)-5-nitrothiazole)
PtCl$_2$(morpholino)(2-amino-5-nitrothiazole)
PtCl$_2$(morpholino)(4-nitrothiazole)
PtCl$_2$(morpholino)(5-i-butyl-2-nitrothiazole)
PtCl$_2$(morpholino)(2-ethoxy-4-nitrothiazole)
PtCl$_2$(morpholino)(2-ethoxy-5-nitrothiazole)
PtCl$_2$(morpholino)(4-dimethylamino-2-nitrothiazole)
PtCl$_2$(morpholino)(2-t-butoxy-5-nitrothiazole)
PtCl$_2$(morpholino)(5-(4-ethylhexyl)-2-nitrothiazole)
PtCl$_2$(morpholino)(4-ethylamino-5-nitrothiazole)
PtCl$_2$(morpholino)(4-(4-amino-n-butyl)-5-nitrothiazole)
PtCl$_2$(morpholino)(2-(6-amino-n-hexyl)-5-nitrothiazole)
PtCl$_2$(cyclohexylamino)(2-amino-5-nitrothiazole)
PtCl$_2$(cyclohexylamino)(4-nitrothiazole)
PtCl$_2$(cyclohexylamino)(5-i-butyl-2-nitrothiazole)
PtCl$_2$(cyclohexylamino)(2-ethoxy-4-nitrothiazole)
PtCl$_2$(cyclohexylamino)(2-ethoxy-5-nitrothiazole)
PtCl$_2$(cyclohexylamino)(4-dimethylamino-2-nitrothiazole)
PtCl$_2$(cyclohexylamino)(2-t-butoxy-5-nitrothiazole)
PtCl$_2$(cyclohexylamino)(5-(4-ethylhexyl)-2-nitrothiazole)
PtCl$_2$(cyclohexylamino)(4-ethylamino-5-nitrothiazole)
PtCl$_2$(cyclohexylamino)(4-(4-amino-n-butyl)-5-nitrothiazole)
PtCl$_2$(cyclohexylamino)(2-(6-amino-n-hexyl)-5-nitrothiazole)
PtCl$_2$(ammine)(2-dimethylamino-5-nitroimidazole)
PtCl$_2$(ammine)(4-i-propoxy-2-nitroimidazole)
PtCl$_2$(ammine)(2-ethyl-4-nitroimidazole)
PtCl$_2$(ammine)(5-n-hexyl-2-nitroimidazole)
PtCl$_2$(ammine)(4-methyl-5-nitroimidazole)
PtCl$_2$(ammine)(4-nitroimidazole)
PtCl$_2$(ammine)(2-nitroimidazole)
PtCl$_2$(ammine)(5-nitroimidazole)
PtCl$_2$(ammine)(5-hydroxy-2-nitroimidazole)
PtCl$_2$(ammine)(4-(4-amino-n-butyl)-5-nitroimidazole)
PtCl$_2$(ammine)(2-(6-amino-n-hexyl)-5-nitroimidazole)
PtCl$_2$(ammine)(6-nitroquinoline)
PtCl$_2$(ammine)(5-nitroquinoline)
PtCl$_2$(diethylamino)(2-dimethylamino-5-nitroimidazole)
PtCl$_2$(diethylamino)(4-i-propoxy-2-nitroimidazole)
PtCl$_2$(diethylamino)(2-ethyl-4-nitroimidazole)
PtCl$_2$(diethylamino)(5-n-hexyl-2-nitroimidazole)
PtCl$_2$(diethylamino)(4-methyl-5-nitroimidazole)
PtCl$_2$(diethylamino)(4-nitroimidazole)
PtCl$_2$(diethylamino)(2-nitroimidazole)
PtCl$_2$(diethylamino)(5-nitroimidazole)
PtCl$_2$(diethylamino)(5-hydroxy-2-nitroimidazole)
PtCl$_2$(dimethylamino)(4-(4-amino-n-butyl)-5-nitroimidazole)
PtCl$_2$(dimethylamino)(2-(6-amino-n-hexyl)-5-nitroimidazole)
PtCl$_2$(dimethylamino)(6-nitroquinoline)
PtCl$_2$(dimethylamino)(5-nitroquinoline)
PtCl$_2$(morpholino)(2-dimethylamino-5-nitroimidazole)
PtCl$_2$(morpholino)(4-i-propoxy-2-nitroimidazole)
PtCl$_2$(morpholino)(2-ethyl-4-nitroimidazole)
PtCl$_2$(morpholino)(5-n-hexyl-2-nitroimidazole)
PtCl$_2$(morpholino)(4-methyl-5-nitroimidazole)
PtCl$_2$(morpholino)(4-nitroimidazole)
PtCl$_2$(morpholino)(2-nitroimidazole)
PtCl$_2$(morpholino)(5-nitroimidazole)
PtCl$_2$(morpholino)(5-hydroxy-2-nitroimidazole)
PtCl$_2$(morpholino)(4-(4-amino-n-butyl)-5-nitroimidazole)
PtCl$_2$(morpholino)(2-(6-amino-n-hexyl)-5-nitroimidazole)
PtCl$_2$(morpholino)(6-nitroquinoline)
PtCl$_2$(morpholino)(5-nitroquinoline)
PtCl$_2$(cyclohexylamino)(2-dimethylamino-5-nitroimidazole)
PtCl$_2$(cyclohexylamino)(4-i-propoxy-2-nitroimidazole)
PtCl$_2$(cyclohexylamino)(2-ethyl-4-nitroimidazole)
PtCl$_2$(cyclohexylamino)(5-n-hexyl-2-nitroimidazole)
PtCl$_2$(cyclohexylamino)(4-methyl-5-nitroimidazole)
PtCl$_2$(cyclohexylamino)(4-nitroimidazole)
PtCl$_2$(cyclohexylamino)(2-nitroimidazole)
PtCl$_2$(cyclohexylamino)(5-nitroimidazole)
PtCl$_2$(cyclohexylamino)(5-hydroxy-2-nitroimidazole)
PtCl$_2$(cyclohexylamino)(4-(4-amino-n-butyl)-5-nitroimidazole)
PtCl$_2$(cyclohexylamino)(2-(6-amino-n-hexyl)-5-nitroimidazole)
PtCl$_2$(cyclohexylamino)(6-nitroquinoline)
PtCl$_2$(cyclohexylamino)(5-nitroquinoline)
PtCl$_2$(ammine)(3-amino-5-nitroisothiazole)
PtCl$_2$(ammine)(4-nitroisothiazole)
PtCl$_2$(ammine)(5-i-butyl-3-nitroisothiazole)
PtCl$_2$(ammine)(3-ethoxy-4-nitroisothiazole)
PtCl$_2$(ammine)(3-ethoxy-5-nitroisothiazole)
PtCl$_2$(ammine)(4-dimethylamino-3-nitroisothiazole)
PtCl$_2$(ammine)(3-t-butoxy-5-nitroisothiazole)
PtCl$_2$(ammine)(5-(4-ethylhexyl)-3-nitroisothiazole)
PtCl$_2$(ammine)(4-ethylamino-5-nitroisothiazole)
PtCl$_2$(ammine)(4-(4-amino-n-butyl)-5-nitroisothiazole)
PtCl$_2$(ammine)(3-(6-amino-n-hexyl)-5-nitroisothiazole)
PtCl$_2$(dimethylamino)(3-amino-5-nitroisothiazole)
PtCl$_2$(dimethylamino)(4-nitroisothiazole)
PtCl$_2$(dimethylamino)(5-i-butyl-3-nitroisothiazole)
PtCl$_2$(dimethylamino)(3-ethoxy-4-nitroisothiazole)
PtCl$_2$(dimethylamino)(3-ethoxy-5-nitroisothiazole)
PtCl$_2$(dimethylamino)(4-dimethylamino-3-nitroisothiazole)
PtCl$_2$(dimethylamino)(3-t-butoxy-5-nitroisothiazole)
PtCl$_2$(dimethylamino)(5-(4-ethylhexyl)-3-nitroisothiazole)
PtCl$_2$(dimethylamino)(4-ethylamino-5-nitroisothiazole)
PtCl$_2$(dimethylamino)(4-(4-amino-n-butyl)-5-nitroisothiazole)
PtCl$_2$(dimethylamino)(3-(6-amino-n-hexyl)-5-nitroisothiazole)
PtCl$_2$(morpholino)(3-amino-5-nitroisothiazole)
PtCl$_2$(morpholino)(4-nitroisothiazole)
PtCl$_2$(morpholino)(5-i-butyl-3-nitroisothiazole)
PtCl$_2$(morpholino)(3-ethoxy-4-nitroisothiazole)
PtCl$_2$(morpholino)(3-ethoxy-5-nitroisothiazole)
PtCl$_2$(morpholino)(4-dimethylamino-3-nitroisothiazole)
PtCl$_2$(morpholino)(3-t-butoxy-5-nitroisothiazole)
PtCl$_2$(morpholino)(5-(4-ethylhexyl)-3-nitroisothiazole)
PtCl$_2$(morpholino)(4-ethylamino-5-nitroisothiazole)
PtCl$_2$(morpholino)(4-(4-amino-n-butyl)-5-nitroisothiazole)

PtCl₂(morpholino)(3-(6-amino-n-hexyl)-5-nitroisothiazole)
PtCl₂(cyclohexylamino)(3-amino-5-nitroisothiazole)
PtCl₂(cyclohexylamino)(4-nitroisothiazole)
PtCl₂(cyclohexylamino)(5-i-butyl-3-nitroisothiazole)
PtCl₂(cyclohexylamino)(3-ethoxy-4-nitroisothiazole)
PtCl₂(cyclohexylamino)(3-ethoxy-5-nitroisothiazole)
PtCl₂(cyclohexylamino)(4-dimethylamino-3-nitroisothiazole)
PtCl₂(cyclohexylamino)(3-t-butoxy-5-nitroisothiazole)
PtCl₂(cyclohexylamino)(5-(4-ethylhexyl)-3-nitroisothiazole)
PtCl₂(cyclohexylamino)(4-ethylamino-5-nitroisothiazole)
PtCl₂(cyclohexylamino)(4-(4-amino-n-butyl)-5-nitroisothiazole)
PtCl₂(cyclohexylamino)(3-(6-amino-n-hexyl)-5-nitroisothiazole)
PtCl₂(ammine)(3-dimethylamino-5-nitropyrazole)
PtCl₂(ammine)(4-i-propoxy-3-nitropyrazole)
PtCl₂(ammine)(3-ethyl-4-nitropyrazole)
PtCl₂(ammine)(5-n-hexyl-3-nitropyrazole)
PtCl₂(ammine)(4-methyl-5-nitropyrazole)
PtCl₂(ammine)(4-nitropyrazole)
PtCl₂(ammine)(3-nitropyrazole)
PtCl₂(ammine)(5-nitropyrazole)
PtCl₂(ammine)(etanidazole)
PtCl₂(ammine)(5-hydroxy-3-nitropyrazole)
PtCl₂(ammine)(4-(4-amino-n-butyl)-5-nitropyrazole)
PtCl₂(ammine)(3-(6-amino-n-hexyl)-5-nitropyrazole)
PtCl₂(diethylamino)(3-dimethylamino-5-nitropyrazole)
PtCl₂(diethylamino)(4-i-propoxy-3-nitropyrazole)
PtCl₂(diethylamino)(3-ethyl-4-nitropyrazole)
PtCl₂(diethylamino)(5-n-hexyl-3-nitropyrazole)
PtCl₂(diethylamino)(4-methyl-5-nitropyrazole)
PtCl₂(diethylamino)(4-nitropyrazole)
PtCl₂(diethylamino)(3-nitropyrazole)
PtCl₂(diethylamino)(5-nitropyrazole)
PtCl₂(diethylamino)(etanidazole)
PtCl₂(diethylamino)(5-hydroxy-3-nitropyrazole)
PtCl₂(dimethylamino)(4-(4-amino-n-butyl)-5-nitropyrazole)
PtCl₂(dimethylamino)(3-(6-amino-n-hexyl)-5-nitropyrazole)
PtCl₂(morpholino)(3-dimethylamino-5-nitropyrazole)
PtCl₂(morpholino)(4-i-propoxy-3-nitropyrazole)
PtCl₂(morpholino)(3-ethyl-4-nitropyrazole)
PtCl₂(morpholino)(5-n-hexyl-3-nitropyrazole)
PtCl₂(morpholino)(4-methyl-5-nitropyrazole)
PtCl₂(morpholino)(4-nitropyrazole)
PtCl₂(morpholino)(3-nitropyrazole)
PtCl₂(morpholino)(5-nitropyrazole)
PtCl₂(morpholino)(etanidazole)
PtCl₂(morpholino)(5-hydroxy-3-nitropyrazole)
PtCl₂(morpholino)(4-(4-amino-n-butyl)-5-nitropyrazole)
PtCl₂(morpholino)(3-(6-amino-n-hexyl)-5-nitropyrazole)
PtCl₂(cyclohexylamino)(3-dimethylamino-5-nitropyrazole)
PtCl₂(cyclohexylamino)(4-i-propoxy-3-nitropyrazole)
PtCl₂(cyclohexylamino)(3-ethyl-4-nitropyrazole)
PtCl₂(cyclohexylamino)(5-n-hexyl-3-nitropyrazole)
PtCl₂(cyclohexylamino)(4-methyl-5-nitropyrazole)
PtCl₂(cyclohexylamino)(4-nitropyrazole)
PtCl₂(cyclohexylamino)(3-nitropyrazole)
PtCl₂(cyclohexylamino)(5-nitropyrazole)
PtCl₂(cyclohexylamino)(etanidazole)
PtCl₂(cyclohexylamino)(5-hydroxy-3-nitropyrazole)
PtCl₂(cyclohexylamino)(4-(4-amino-n-butyl)-5-nitropyrazole)
PtCl₂(cyclohexylamino)(3-(6-amino-n-hexyl)-5-nitropyrazole)

and the corresponding bromides, nitrates, pyruvates, acetates, malonates, ethyl malonates, oxalates, phthalates, and 1,1-cyclobutane dicarboxylates.

To the foregoing list, which includes the compounds of Formula (1), is added the corresponding list of compounds of Formula (2) wherein each entry has the formula $$PtCl(ammine)_2L^+Y^-$$

$$PtCl(dimethylamino)_2L^+Y^-$$

$$PtCl(morpholino)_2L^+Y^-$$

$$PtCl(cyclohexylamino)_2L^+Y^-$$

in place of the moieties shown. For these compounds of Formula (2), each NHR₂ ligand is independent; also included are, e.g., PtCl(ammine)(morpholino)L, PtCl(morpholino)(cyclohexylamino)L, etc. Nitrate is preferred for Y⁻.

SYNTHESIS OF THE INVENTION COMPOUNDS

The compounds of formula (1) are synthesized from the monoammine of Pt(II) of the formula K[PtCl₃(NH₃)] by reaction of one equivalent of the radiosensitizing ligand in aqueous solution, according to the scheme:

$$K[PtCl_3(NH_3)] + L \rightleftarrows Pt(L)(NH_3)Cl_2 + KCl$$

The reaction is allowed to proceed for 10-36, preferably 12-24, hours, and the complex formed may be recovered by evaporation of the solvent and crystallization. The resulting compounds of Formula (1) are mono-substituted with L, and are predominantly in the cis form. The trans form is obtained by redissolving in a suitable solvent, such as ethanol, and permitting isomerization to take place.

The compounds of Formula (2) are prepared by treatment of the dichloro diamine with the radiosensitizing ligand in the presence of silver nitrate, according to the reaction $$[PtCl_2(NH_3)_2] + L + Ag^+ \rightleftarrows [PtCl(NH_3)_2L]^+ + AgCl.$$

The AgCl is removed by filtration and the complex recovered by evaporation of solvent and crystallization.

FORMULATION AND ADMINISTRATION

The platinum complexes of Formulas (1) and (2) mono-substituted with radiosensitizers are useful either for direct chemotherapy or to sensitize hypoxic tumor cells in warmblooded animal hosts to radiation or to other drugs. While humans are the subject of most concern, the compounds of the invention are also useful in treatment of animal subjects such as farm animals, sports animals, and pets.

For use as radiosensitizers, the compounds are administered to subjects wither systemically or locally. Systemic administration may be oral or parenteral, and typically intravenous administration is preferred. For parenteral administration, the compounds of Formulas (1) or (2) are generally prepared in a unit dosage-injectable form as a solution, emulsion, suspension, as so forth with a pharmaceutically acceptable excipient. Excipients and formulations are known in the art and are summarized, for example, in *Remington's Pharmaceutical Sciences*, Mack Publishing Company, Easton, Pa., latest edition. Examples of excipients include water, buffer, saline, Ringer's solution, dextrose, and Hanks' solution. Nonaqueous vehicles may also be included, such as peanut or cottonseed oil, or single compounds such a triglycerides or fatty acid esters. Additional substances such as stabilizers, buffers, antioxidants, and preservatives may also be included in the composition.

Oral administration may be by capsule or pill or powder, and may contain additional diluents such as lactose, maltose, starch, gelatin, sorbitan, and magnesium stearate.

The amount of compound administered is sufficient to sensitize the target cells, but less than an amount toxic to the organism. The amount will depend, of course, on the individual subject, the tumor being treated, the protocol for radiation, and the judgment of the practitioner. In-most radiation protocols, a fractionated radiation dosage is given over a period of several days, weeks, or months, and the compounds of the invention are administered in conjunction with the radiation. They are administered at a time such that their peak concentration in the hypoxic cells occurs at the time radiation treatment is administered. Clearly, the timing of this administration is subject to considerable variation, depending, for example, on the dosage form and the location of the tumor. Individual protocols should be designed for particular situations and individual patients, but such design is well within the skill of the practitioner of the art, and requires little in the way of calibration and verification.

In view of the foregoing, it is difficult to estimate a generalized dosage, but most protocols will be effective with dosages in the range of 0.01-20 mmol of the radiosensitizing compounds per kg of subject's weight.

Exemplary carcinomas and sarcomas which are susceptible to radiosensitization include carcinomas of the intestines, liver, lung, skin, and cervix, and sarcomas such as Ewing's, lymphatic, Jensen's, Karposi's, and the like.

For use in chemotherapy, the compounds are administered in accordance with usual procedures for drug administration and formulation, such as those set forth in *Remington's Pharmaceutical Sciences*, referenced above.

Chemotherapeutic protocols are aided by the introduction into the protocol of a suitable vasoactive agent, such as 5-hydroxytrypamine (5-HT) or hydralazine, preferably hydralazine. It has been shown, for example, that the amount of RSU-1069 required for effectiveness can be reduced by administration of 5-hydroxytryptamine or hydralazine (Chaplin, D. J., et al, *Brit J Cancer* (1986) 54:727-731; Horwich, A., et al, *Brit J Radiol* (1986) 59:1238-1240). RSU-1069 is a compound sometimes used for chemotherapy and having a high incidence of side effects. The reagents noted are effective in reducing blood flow to tumors without affecting normal tissue blood flow. Other vasoactive agents could also be used.

The compounds of the invention also show enhanced activity in cytotoxicity to hypoxic cells in the presence of vasoactive agents. The administration of such agents can further reduce the oxygenation of tumors, and thereby intensify the cyctotoxic effects of agents which are selective for hypoxic cells. Accordingly, in a preferred method, the compounds of the invention are administered to the subject at reduced dosage levels, along with an effective amount of 5-HT or hydralazine, or of other suitable vasoactive agents which selectively reduce blood flow to tumors.

Typical dosages of the compounds of the invention for chemotherapeutic use without the administration of the vasoactive agent are in the range of approximately 0.1-5 mg/kg. Reductions in dosage levels of approximately ten-fold may be achieved by coadministration of appropriate vasoactive agents. Conversely, the efficacy of the inventive compounds can be improved by coadministration with vasoactive agents at the same dosage levels.

Tumors susceptible to chemotherapeutic treatment with the compounds of the invention in either the presence or absence of vasoactive agents are hypoxic solid tumors, and include a list of specific tumor types similar to that set forth above for the radiosensitizing protocols.

In addition, the compounds of the invention are useful for radioimaging of hypoxic tumors. The compounds are combined with a scintographic label, such as $^{99}Tc$, $^{131}I$, or $^{111}n$ using standard labeling techniques, and the labeled complexes administered systemically. The labeled complexes home to the location of the hypoxic cells and can be detected using conventional scanning techniques such as those described in Franco, H., et al, *Int J Radiat Onco Biol Phys* (1986) 12:1195-1202.

EXAMPLES

The following examples are intended to illustrate but not to limit the invention.

EXAMPLE 1

Preparation of Cis and Trans Mono-MISO

One equivalent of misonidazole (205 mg, 1 mM) was added to a solution of $K[PtCl_3(NH_3)]$, (358.35 mg, 1 mM), dissolved in the minimum volume of $H_2O$ using an equal volume of hot $H_2O$ (The starting material $K[PtCl_3(NH_3)]$ was prepared from $K_2PtCl_4$ according to the method of Abrams, M. et al, *Inorganic Chemistry* (in press), but may be prepared by other known methods.)

The mixture was then heated until all the nitroimidazole ligand was dissolved, during which time the solution color changed from yellow to orange. The solution was then stirred for approximately 24 hr at room temperature and evaporated to dryness. The resultant orange oil was dissolved in acetone and the solution filtered to remove KCl.

The filtrate was dried over anhydrous $CaCl_2$, filtered again, and evaporated to dryness. The residue was treated with diethyl ether to give the yellow-orange product $PtCl_2(NH_3)$ (misonidazole) (mono-MISO), yield 60%, which was designated as cis based on IR spectral data Elemental analysis: %C, 17.40 (17.35); %H, 3.02 (2.89); %N, 11.39 (11.57).

To obtain the trans configuration, the orange solid was dissolved in EtOH by gentle warming. Upon dissolution, the initial orange color changed to yellow-green and, upon cooling, a yellow product, which was the trans configuration based on IR spectral data, which precipitates out at 50% yield. Elemental analysis: %C, 17.32 (17.35); %H, 2.93 (2.89); %N, 10.99 (11.57); %Cl, 15.57 (14.67). MW =488 (calc: 484).

The IR spectrum for the cis configuration showed a broad band with maxima at 338 and 332 cm$^{-1}$. The trans configuration showed a sharper band at 330 cm$^{-1}$, different from the cis configuration. Other differences were also observed. The trans compound shows extra bands at 2400-3500 cm$^{-1}$.

EXAMPLE 2

Preparation of Mono-METRO

In a manner exactly analogous to that set forth in Example 1, but substituting for misonidazole, metronidazole, the cis form of mono-METRO was prepared in 55% yield. Elemental analysis: %C, 15.76 (15.86); %H, 2.31 (2.64); %N, 12.06 (12.33); %Cl, 15.95 (15.62). Molecular weight in methanol, 429 (calc. 453). A broad band for (PtCl) with maxima at 339 and 331 cm$^{-1}$ was obtained in the IR spectrum.

In a manner similar to that set forth in Example 1, the cis-isomer was dissolved in ethanol and warmed to convert at least a portion of the material to the trans form, which was recovered as described in Example 1.

EXAMPLE 3

Preparation of Mono-NI

In a manner similar to that set forth in Example 1, but substituting 4-nitroimidazole for misonidazole, the cis-platinum complex coordinated with one ligand of 4-nitroimidazole (mono-NI) was obtained, and characterized by elemental analysis as: %C, 8.33 (9.09); %H, 1.32 (1.5); %N, 10.84 (10.6).

EXAMPLE 4

Preparation of Mono-ANT

In a manner precisely similar to that set forth in Example 1, but substituting for misonidazole 2-amino-5-nitrothiazole, the corresponding cis and trans forms of mono-ANT were prepared.

EXAMPLE 5

Comparison of Toxicity in Hypoxic and Aerated Cells

The toxicity of the invention compounds with respect to Chinese hamster ovary (CHO) cells was compared in air and in nitrogen induced hypoxia as described by Moore, B. A., et al, *Radiation Research* (1976) 67:459-478. The radiosensitizing ligands, or cis or trans-dichlorodiamine platinum II (DDP) or the bisubstituted platinum complexes, PtCl$_2$(L)$_2$, were used as controls.

The cells were carried in MEM a medium with 10% fetal calf serum, and plating efficiencies were determined on the seventh day after plating.

Figure 1:
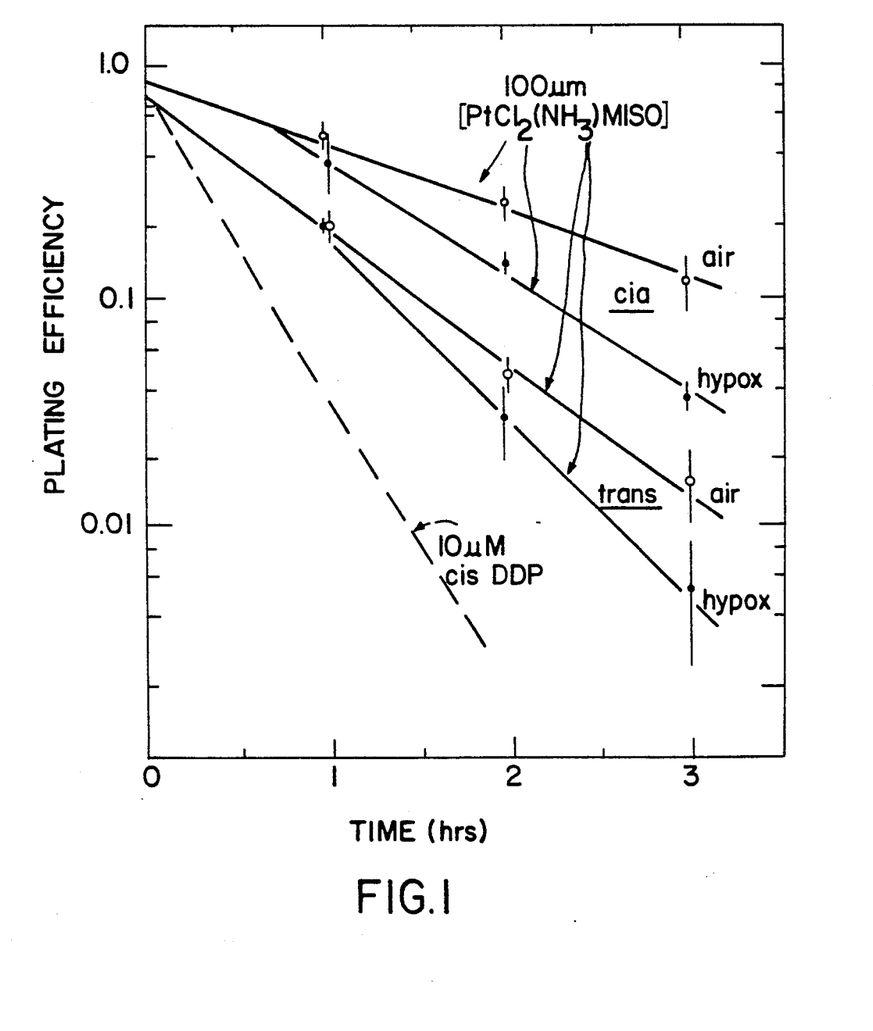
FIG. 1 shows the concentration dependence of radiosensitization by certain compounds of the invention.

In one set of experiments, the toxicity of the cis and trans-mono-MISO complexes was determined at 100 mM/dm$^3$ in aerobic and hypoxic cells. These results are shown in FIG. 1. It is clear from FIG. 1 that toxicity is greater in hypoxia than in air, and that the trans isomer is more toxic than cis. Either complex is more toxic than MISO alone, although less toxic than cisDDP, as indicated by the dashed line for cis-DDP at 10 mM/dm$^3$.

In similar experiments at 100 mM/dm$^3$, MISO and trans-[PtCl$_2$(miso)$_2$] show no toxicity. Survival rates for trans-DDP and monoammine were 0.2 and 0.1 respectively. Thus, cis-DDP and the monoammine were somewhat more toxic than the compounds of the invention; trans-[PtCl$_2$(miso)$_2$] and trans-DDP are somewhat less toxic. The approximate order of hypoxic toxicity of platinum complexes is cis-DDP ff trans-mono-MISO f monoammine Z cis-mono-MISO f trans-DDP f mono-METRO Z mono-NI f mono-ANT. The order of toxicity of free ligand is 4-nitroimidazole f MISO f ANT f METRO.

Figure 5:
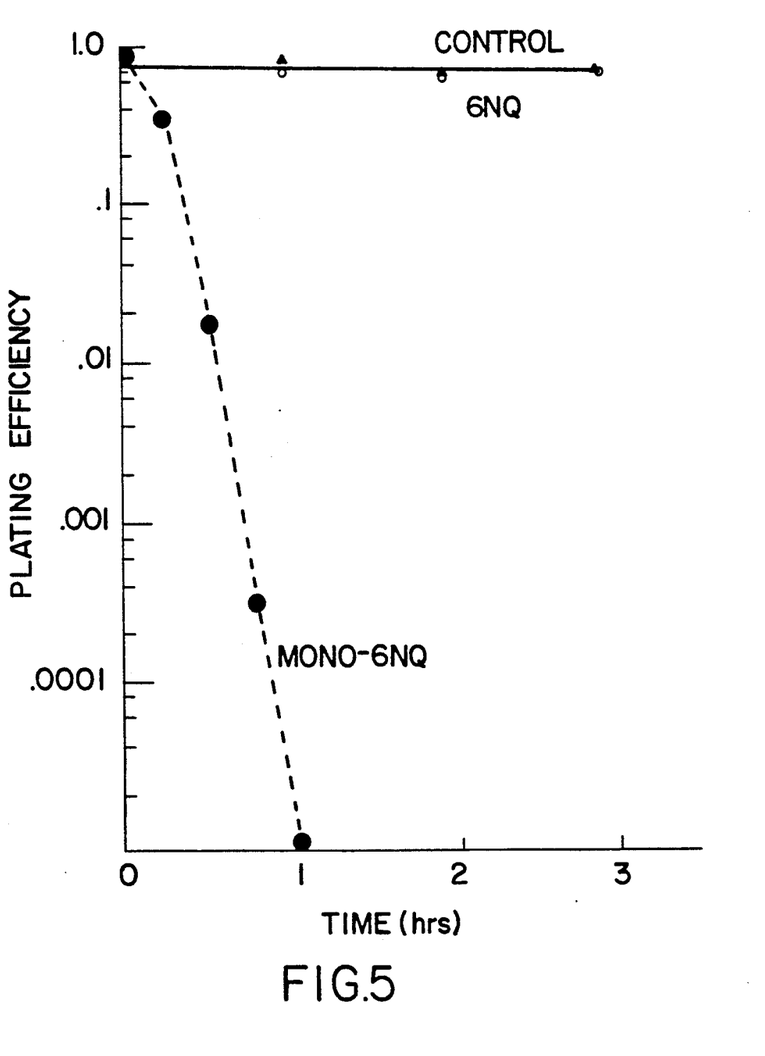
FIG. 5 is a graph showing the toxicity of the invention compound [PtCl$_2$(NH$_3$)(6-nitroquinoline)] as compared to 6-nitroquinoline alone.

In similar experiments using the corresponding 6-nitroquinoline compound, [PtCl$_2$(NH$_3$)(6NQ)], (mono-6NQ), the complex showed much higher toxicity than 6NQ alone, as demonstrated in FIG. 5. Using 100 mM levels, mono-6NQ caused plating efficiency to drop to 0 after an hour, while 6NQ had no effect after 3 hours.

EXAMPLE 6

Radiosensitization of CHO Cells

Radiosensitization of CHO cells was determined as described by Moore, B. A., et al, sucra, at 4° C., except that the cells were incubated with complex for 1 hr at 37° C. to allow binding to DNA prior to radiation. A Picker X-ray source (250 kVp, 1.7 mm Cu) was used. As with the toxicity studies, cells were carried, irradiated, and plated in MEM a medium with 10% fetal calf serum, and plating efficiencies were determined on the seventh day after plating. Enhancement ratios (ER) were calculated from the doses required to reduce survival to 1%.

Figure 2:
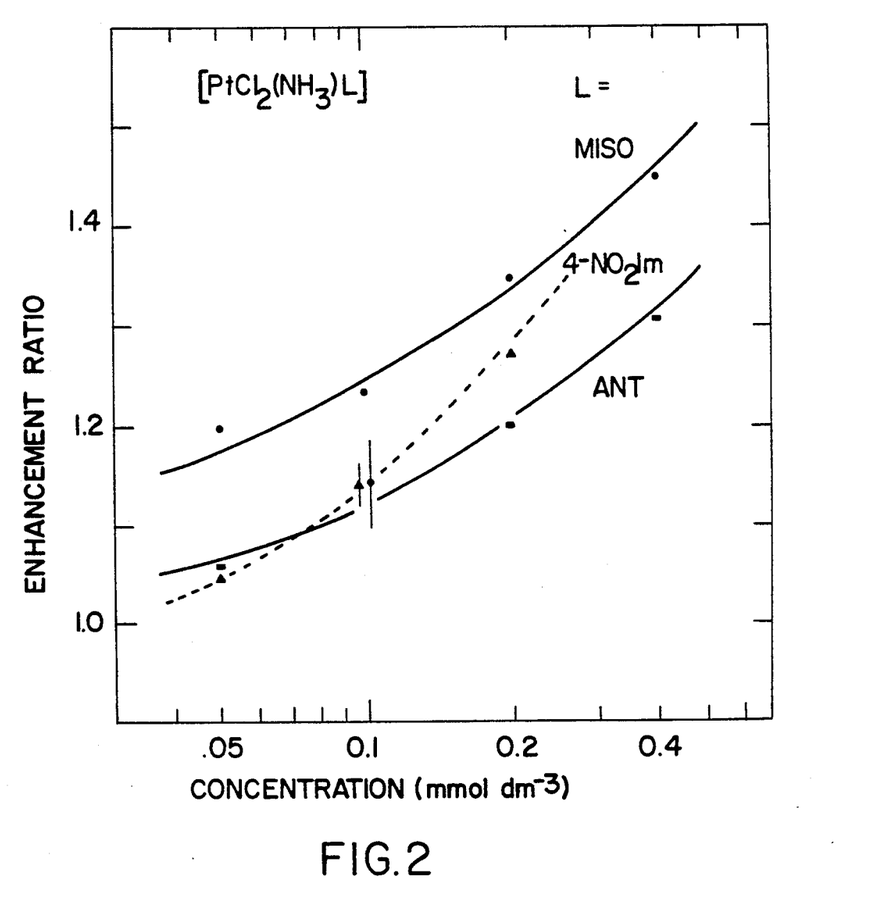
FIG. 2 shows the direct toxicity of two compounds of the invention to hypoxic cells in comparison to their toxicity to aerated cells.

FIG. 2 shows the results obtained for three compounds of the invention, mono-MISO, mono-NI, and mono-ANT, all in the cis configuration at various concentrations. Mono-MISO was somewhat more effective than mono-NI, which was somewhat more effective than mono-ANT. Mono-METRO, not shown in the graph, was approximately equal to mono-ANT. At 100 mM/dm$^3$, the alone); mono-NI gave 1.16 (vs. 1.10 for ligand alone); mono-ANT gave 1.15 (vs. 1.25 for ligand alone). Sensitization was also tested in oxygen for the various compounds, and no sensitization was obtained by trans-bis-MISO, MISO alone, or cis-mono-MISO.

Table 1 summarizes the results at various concentrations for the compounds tested.

TABLE 1

| | mmol/dm$^3$ | ER |
|---|---|---|
| Monoammine | 100 | 1.2 |
| cis-mono-MISO | 100 | 1.25 |
| trans-mono-MISO | 100 | 1.25 |
| trans-bis-MISO | 100 | 1.2 |
| trans-DDP | 100 | 1.3 |
| cis-DDP | 10 | 1.3 |
| MISO | 100 | 1.3 |
| | 250 | 1.4 |

Figure 7:
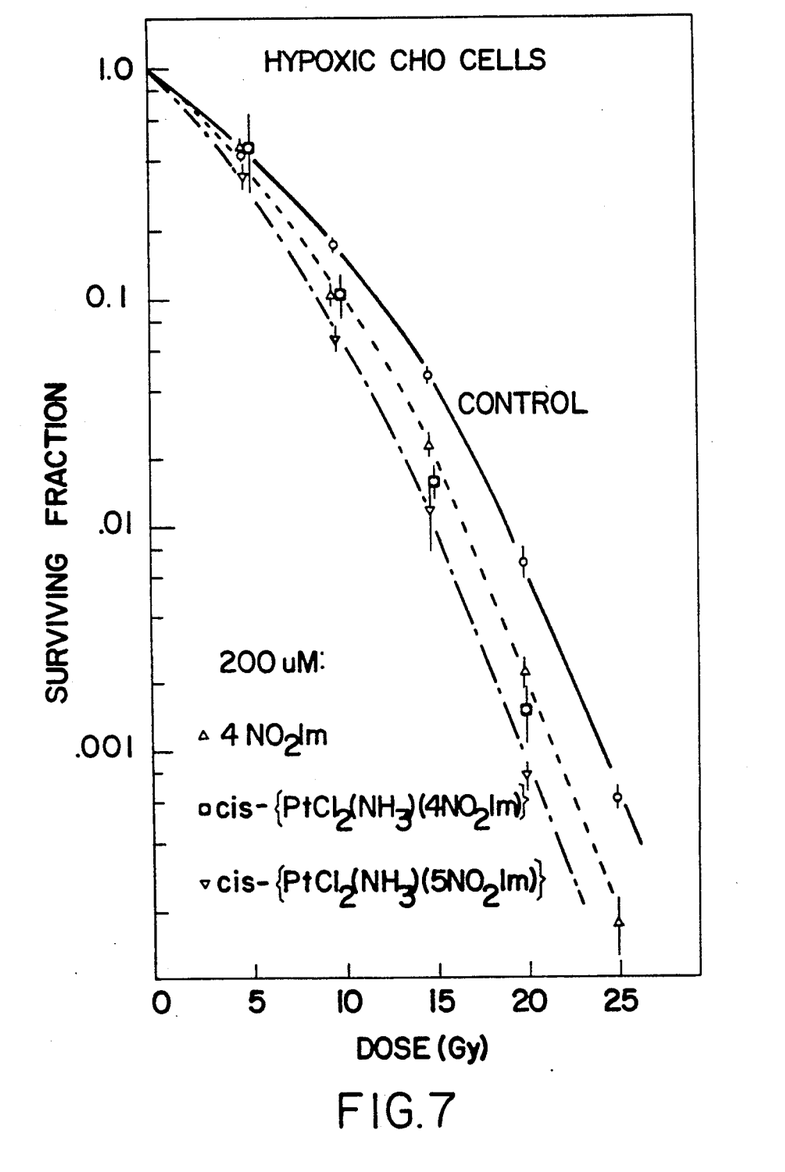
FIG. 7 is a graph showing radiosensitization of CHO cells by mono-4NI and mono-5NI.

The ability of cis-mono-4NI and of cis-mono-5NI to radiosensitize CHO cells in comparison with free 4(5)-nitroimidazole is shown in FIG. 7. The enhancement ratio (ER) was higher for mono-5NI than for mono-4NI (1.28 as compared to 1.16).

Figure 6:
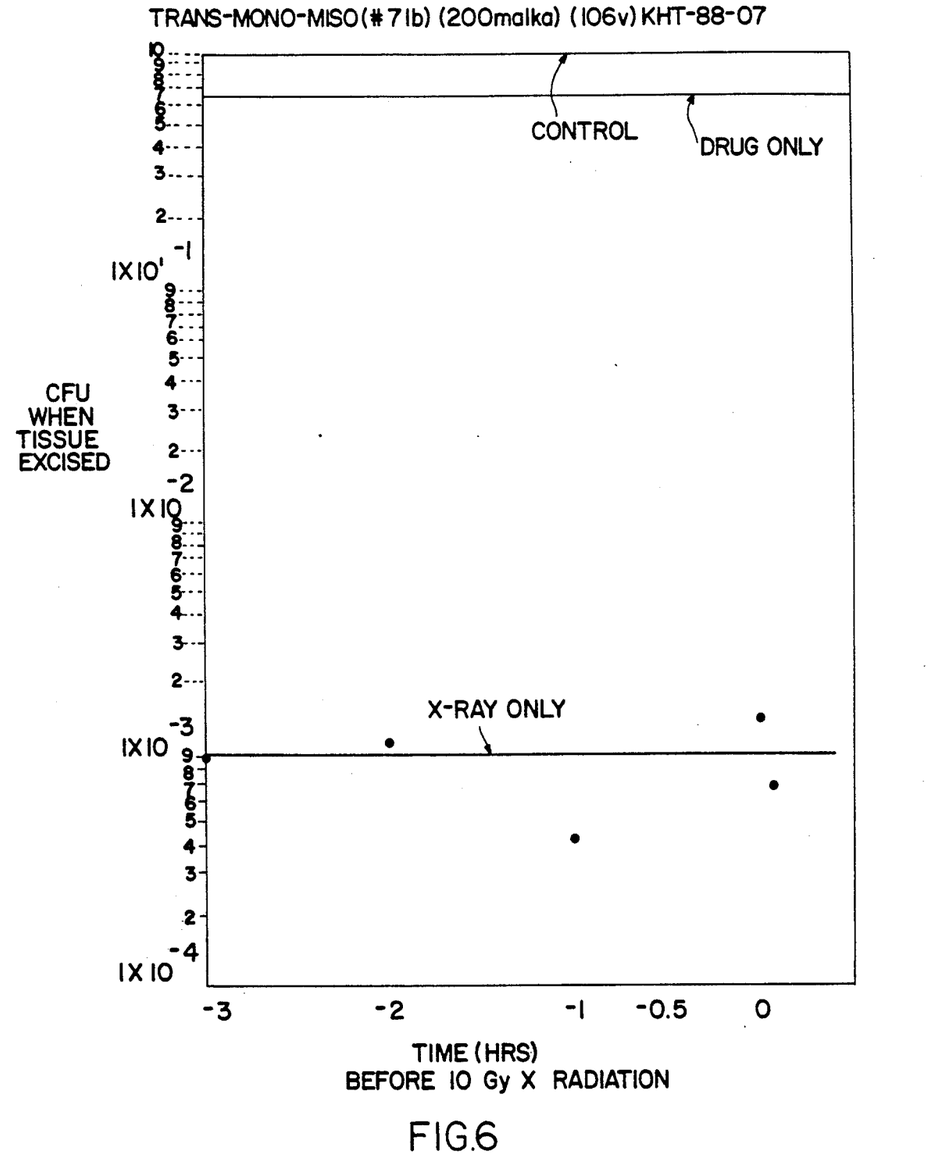
FIG. 6 is a graph showing the radiosensitizing effect in vivo of the invention compound mono-MISO.

Radiosensitization by mono-MISO was also shown in vivo in the KHT tumor model using 200 mg/kg of trans mono-MISO administered 3, 2, 1, ½ or 0 hours prior to X-irradiation. The results shown in FIG. 6, indicate drug administered 0.5 or 1 hour prior to irradiation enhance the effect of the X-rays.

EXAMPLE 7

Binding to DNA

The ability of the invention compounds to bind DNA was tested using an assay which is based on inhibition of the ability of restriction enzymes to cleave the complexed DNA. The substrate in the assay was the plasmid pSV2-gpt (Mulligan, R., et al *Science* (1980) 209:1422–1427). After growth in *E. coli* this 5.2 kb plasmid was extracted and linearized using PvuII. Cleavage of the extracted linearized segment by BamHI or EcoRI results in two fragments per enzyme. Inhibition of this cleavage by test compounds provides an assay method for binding of the test compounds.

In the assay, DNA (20 mg/ml) in 100 mM Tris-HCl, 1 mM EDTA, pH 8, was treated with the test compounds at approximately 100 mM for 1 hr at 37° C. Unbound drug was then removed using a G-50 Sephadex spin column (Pharmacia).

To 30 mM of the treated DNA, 23.5 ml of a buffer solution containing 0.33 M Tris-acetate, pH 7.9, 0.66 M potassium acetate, 0.10 M dithiothreitol, and 1 mg/ml BSA, along with 10 units of enzyme, were added. Enzyme activity was stopped using 1 ml 0.5 M EDTA after 30 min at 37° C. Tracking 0.25% bromophenol blue, 0.25% xylene cyanol in 30% glycerol water) was added, and 10 ml of the resulting solution loaded onto a 1% agarose gel made with E buffer (0.04 M Tris, 5 mM sodium acetate; 1 mM EDTA, pH 7.8) and subjected to horizontal electrophoresis. The slab gel was stained with aqueous ethidium bromide solution (1 ng/ml) and photographed under UV light.

Inhibition of the restriction enzyme cleavage was assessed qualitatively by noting the relative proportion of bands, or quantitatively by analyzing densitometric scans of the negatives of the recorded pictures.

Figure 3:
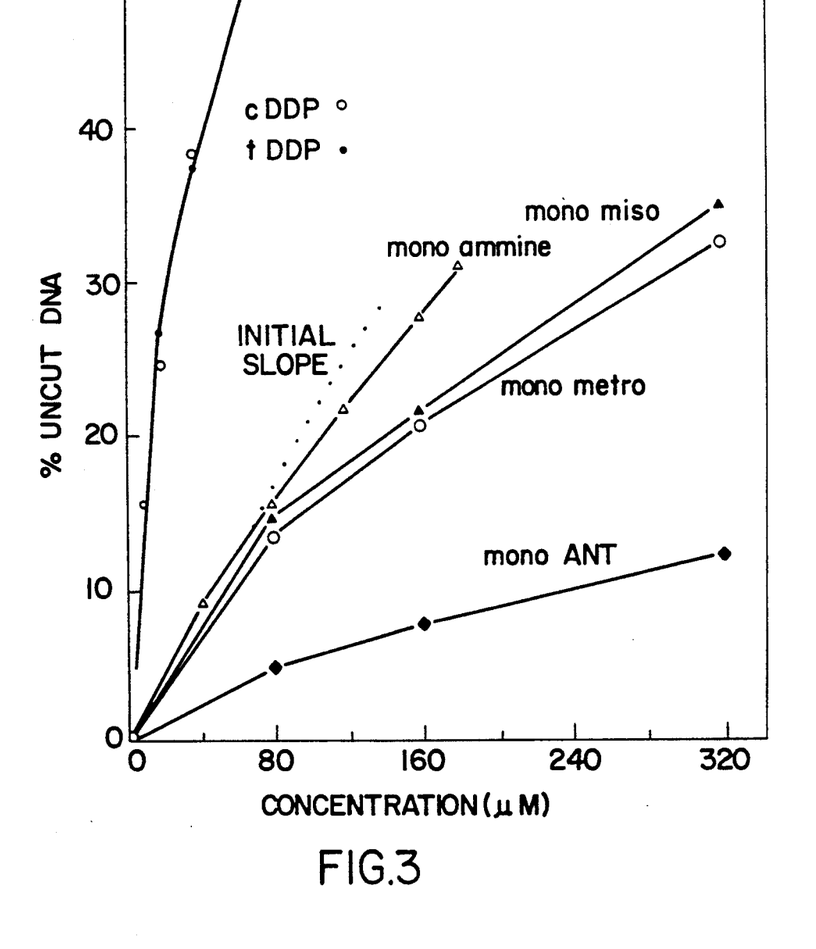
FIG. 3 shows the binding to DNA of compounds of the invention as assessed by inhibition of BamHI cleavage of plasmid DNA.

The controls, cis-DDP and monoammine, showed binding to the DNA as indicated by enzyme inhibition; cis-DDP binds much more strongly than the monoammine. Thus, treatment with only 40 mM cis-DDP results in a 30% inhibition of BamHI cleavage, a level not reached by treatment of the DNA with the monoammine until the concentration was increased to 160 mM. The results for the compounds of the invention are shown in FIG. 3. At least 10% inhibition of cleavage with BamHI was obtained for mono-ANT at 320 mM, but for mono-METRO and mono-MISO this is attained at a much lower concentration of approximately 50 mM.

Figure 8:
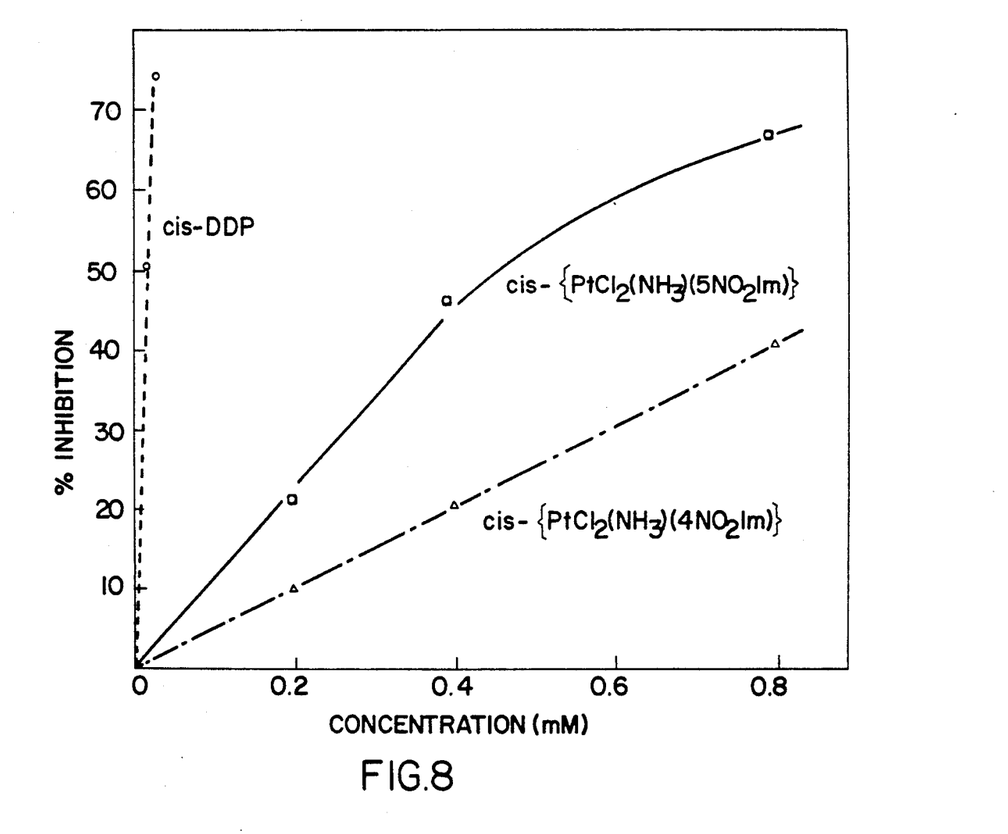
FIG. 8 is a graph showing DNA binding activity of mono-4NI and mono-5NI.

In a similar determination, the results of which are shown in FIG. 8, cis-mono-5NI appeared to show more effective binding to DNA at all concentrations than cis-mono-4NI; neither bound as well, however, as cis-DDP.

These results are consistent with data obtained in whole cells using atomic absorption. In this procedure, after exposure to the test compound for 1–2 hr, $10^9$ CHO cells previous for 18 hr with $^{14}C$ thymidine were washed and their DNA extracted, according to the procedure of Pera, M. F., Jr., et al, *Chem Biol Interact* (1981) 37:245–261, and analyzed for platinum using a Perkin-Elmer Atomic Absorption Spectrometer with a graphite furnace. $^{14}C$ counts were used to normalize the platinum results by counting an aliquot of the hydrolyzate which had been prepared for atomic absorption in liquid scintillation counter and comparing these $^{14}C$ counts to the number of counts per cell. For treatment with the various compounds of the invention at 100 mM, the amount of platinum bound to the extracted DNA was, in ng Pt/$10^6$ cells: 6 for cis-DDP, 5 for trans-DDP, and considerably higher for some of the sensitizer containing platinum complexes. Though the results of this assay were erratic they establish that the Pt complexes cross cell membranes and bind to DNA in mammalian cells.

EXAMPLE 8

Potentiation of Cytotoxicity Using Vasodilators

The effect of the vasodilator hydralazine on the cyctoxicity of the compounds of the invention for toxic cells in vivo was tested using the Lewis lung carcinoma or KHT sarcoma model in C57B1 mice. The protocols were those of Chaplin, D. J. (*Brit J Cancer* (1986) 54:727–731).

Figure 4:
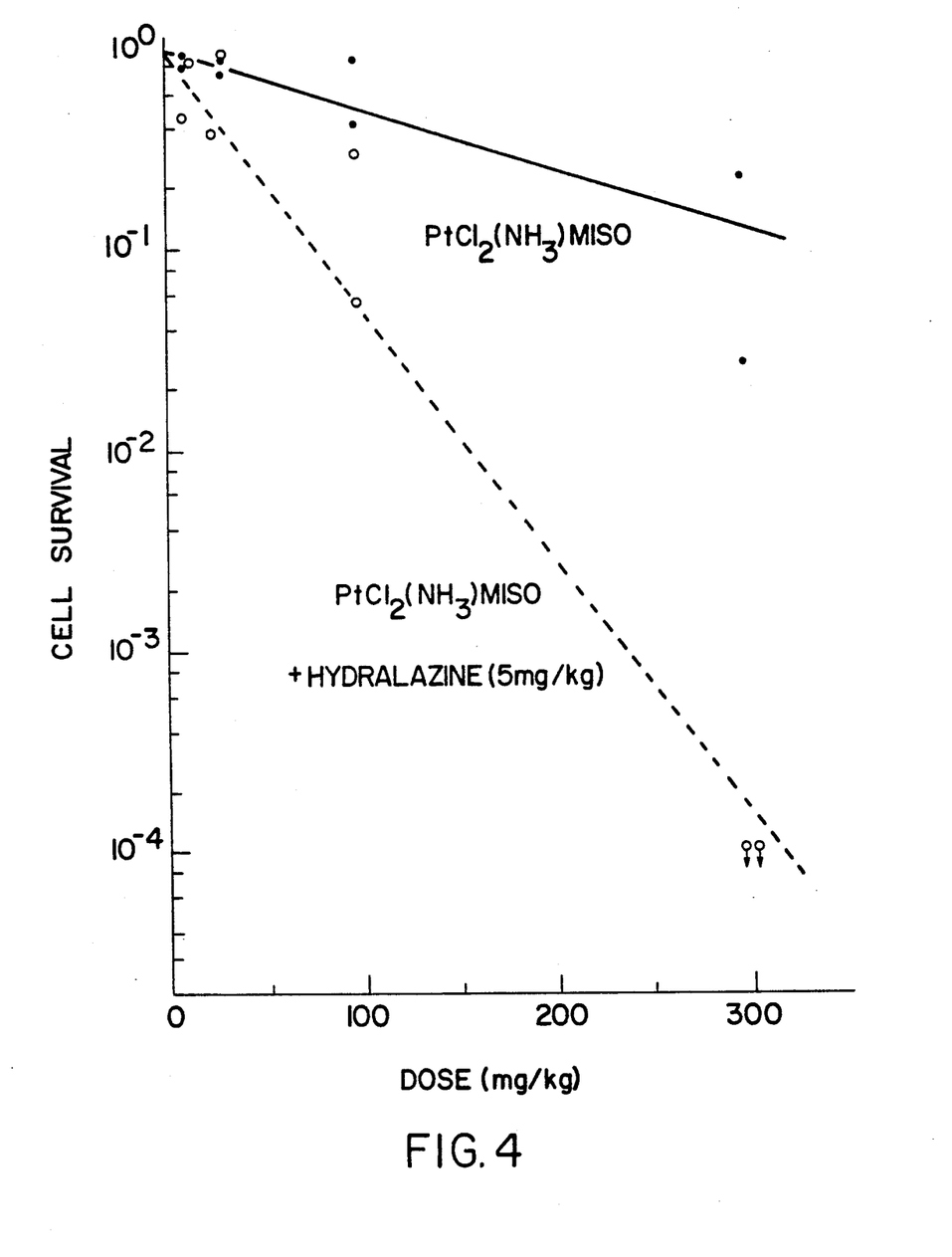
FIG. 4 shows the effect of addition of hydralazine on the ability of mono-MISO to kill tumor cells in animals.

When these procedures were applied to potentiation by hydralazine of RSU-1069 (Chaplin, D. J., et al, *Int J Radiat Oncol Biol Phys* (1987), in press), hydralazine was shown, at levels of 5 mg/kg or 30 mg/kg, to enhance the effect of RSU-1069 administered at 0.1 mg/g IP if administered within three hours of the administration of the RSU-1069. Similar protocols using the invention compound mono-MISO showed potentiating effects of hydralazine on this compound at 5 mg/kg, as shown in FIG. 4. These results pertain to the KHT sarcoma model; mono-MISO was administered at doses between 10 and 300 mg/kg with or without supplement of hydralazine. As indicated in FIG. 4, the cell survival drops drastically (approx. 3 logs) in the presence of the combined therapy. A much lower dose (4×) of the invention compounds are needed to achieve equitoxic doses when hydralazine is coadministered.

EXAMPLE 9

Preparation of [PtCl$_2$(NH$_3$)(6-nitroquinoline)

A. 6-nitroquinoline (0.26 g) was dissolved in 30 ml methanol and added to a solution containing 0.487 g K[PtCl$_3$NH$_3$] in 30 ml of water. The solution was stirred overnight and the next day the yellow precipitate was filtered, washed with water ethanol and ether, and recrystalized from DMF/water.

Elemental analysis: C: 23.6 (calculated: 23.6); H: 1.9 (calculated 1.98); N: 9.1 (calculated: 9.2)

B. PtCl$_2$(NH$_3$) (5-nitroquinoline) was prepared in an identical manner, substituting 5-nitroquinoline for 6-nitroquinoline:

EXAMPLE 10

Preparation of [PtCl(NH$_3$)$_2$(metronidazole)]$^+$NO$_3$$^-$

To a suspension of cis-[PtCl$_2$(NH$_3$)$_2$] in water was added 1 equivalent of metronidazole, also in water, followed by 1 equivalent of AgNO$_3$ in methanol (water to methanol final volume 1:1). The reaction was stirred overnight. The colorless solution was then filtered to remove AgCl and the solution was evaporated to ½ volume. The product title compound was precipitated by addition of acetone.

EXAMPLE 11

Cross-Resistance with Other Drugs

Patients become resistant to cisplatin (cisDDP) and to many related drugs. Several of the invention compounds were tested for toxicity with respect to cisDDP-sensitive and cisDDP-resistant cells (according to the method of Hacker, et al, *Cancer Res* (1985) 45:4748.) As shown in Table 2, these compounds are comparably effective in both, while cisDDP is 50× more effective in "sensitive" cells. The data in Table 2 thus show that the "mono" series do not show cross-resistance.

TABLE 2

| Complex | ID$_{50}$ in L1210 Cells | | |
|---|---|---|---|
| | cDDP sensitive line mM | cDDP resistant line mM | Ratio |
| cis mono MISO | 8.5 | f41 | 5 |
| trans mono MISO | 6.5 | 18.6 | 3 |
| cis mono METRO | 4.4 | f23.12 | 5 |
| cisDDP | 0.1 | 5 | 50 |
| transDDP | 22 | 66 | 3 |

We claim:

1. A pharmaceutical composition for sensitization of hypoxic cells to radiation or for the inhibition of tumor growth in those tumors sensitive to treatment therewith which comprises an effective amount of the compound of the formula:

$$PtX_n(NR_2H)(L) \qquad (1)$$

wherein n is 1 or 2, and wherein when n is 2, X is a monovalent biologically acceptable anion, and when n is 1, X is a divalent biologically acceptable anion;

each R is independently H or alkyl, or both Rs together are a piperidino or morpholino residue; and L is a radiosensitizing ligand selected from a mononitro-substituted imidazole, a mononitro-substituted pyrazole, a mononitro-substituted thiazole and a mononitro-substituted isothiazole, in admixture with a suitable pharmaceutically acceptable excipient.

2. A method to inhibit tumor growth in those tumors sensitive to treatment therewith in animals which comprises administering to an animal in need of such treatment a tumor-inhibiting amount of a compound of the formula:

$$PtX_n(NR_2H)(L) \qquad (1)$$

wherein n is 1 or 2, and wherein when n is 2, X is a monovalent biologically acceptable anion, and when n is 1, X is a divalent biologically acceptable anion;

each R is independently H or alkyl, or both Rs together are a piperidino or morpholino residue; and L is a radiosensitizing ligand selected from a mononitro-substituted imidazole, a mononitro-substituted pyrazole, a mononitro-substituted thiazole and a mononitro-substituted isothiazole or a pharmaceutical composition containing a tumor-inhibiting amount of the compound of formula 1.

3. The method of claim 2 which further includes the administration of a vasoactive agent to said animal.

4. The method of claim 3 wherein the vasoactive agent is hydralazine.

5. A method to inhibit the growth of hypoxic tumors in those tumors sensitive to treatment therewith in a warmblooded animal which method comprises radiosensitizing the hypoxic tumor cells in said animal by administering the compound of the formula:

$$PtX_n(NR_2H)(L) \qquad (1)$$

wherein n is 1 or 2, and wherein when n is 2, X is a monovalent biologically acceptable anion, and when n is 1, X is a divalent biologically acceptable anion;

each R is independently H or alkyl, or both Rs together are a piperidino or morpholino residue; and L is a radiosensitizing ligand selected from a mononitro-substituted imidazole, a mononitro-substituted pyrazole, a mononitro-substituted thiazole and a mononitro-substituted isothiazole to the animal at a dosage that radiosensitizes said cells.

6. The method of claim 5 which further includes irradiating the tumor cells in said animal.

7. The composition of claim 1 wherein L is a mononitro-substituted imidazole, a mononitro-substituted pyrazole, a mononitro-substituted thiazole or a mononitro-substituted isothiazole which is unsubstituted or which is substituted by one $R^1$ group, wherein $R^1$ is selected from alkyl optionally containing an amino substituent, $OR^3$, and $N(R^3)_2$, wherein $R^3$ is H or lower alkyl.

8. The composition of claim 1, wherein L is a mononitro-substituted imidazole or a mononitro-substituted pyrazole and wherein one ring nitrogen is unsubstituted or substituted by an $R^2$ group wherein $R^2$ is alkyl (1–8C) substituted by one or more $—OR^3$ and wherein one or two methylene groups maybe replaced by O.

9. The composition of claim 8 wherein $R^2$ is alkyl of 2–3C mono- or di-substituted with OH and/or $OCH_3$.

10. The composition of claim 9 wherein $R^2$ is $—CH_2CH(OH)CH_2OCH_3$, $—CH_2OCH_2CHOH$, or $—CH_2CH_2OH$.

11. The composition of claim 7 wherein $R^1$ is amino, alkyl, or aminoalkyl.

12. The composition of claim 7 wherein L is selected from misonidazole (MISO), metronidazole (METRO), 4-nitroimadazole (NI), and 2-amino-5-nitrothiazole (ANT).

13. The composition of claim 1 wherein R is H.

14. The composition of claim 12 wherein R is H.

15. The composition of claim 1 wherein X is Cl.

16. The composition of claim 12 wherein X is Cl.

17. The composition of claim 16 which is selected from mono-MISO, mono-METRO, mono-NI, and mono-ANT.

18. The composition of claim 15 which is the trans isomer.

19. The method of claim 16 or 19 wherein L is a mononitro-substituted imidazole, a mononitro-substituted pyrazole, a mononitro-substituted thiazole or a mononitro-substituted isothiazole which is unsubstituted or which is substituted by one $R^1$ group, wherein $R^1$ is selected from alkyl optionally containing an amino substituent, $OR^3$, and $N(R^3)_2$, wherein $R^3$ is H or lower alkyl.

20. The method of claim 16 or 19 wherein L is a mononitro-substituted imidazole or a mononitro-substituted pyrazole and wherein one ring nitrogen is unsubstituted or substituted by an $R^2$ group wherein $R^2$ is alkyl (1–8C) substituted by one or more $—OR^3$ and wherein one or two methylene groups may be replaced by O.

21. The method of claim 20 wherein $R^2$ is alkyl of 2–3C mono- or di-substituted with OH and/or $OCH_3$.

22. The method of claim 21 wherein $R^2$ is $—CH_2CH(OH)CH_2OCH_3$, $—CH_2OCH_2CHOH$, or $—CH_2CH_2OH$.

23. The method of claim 19 wherein $R^1$ is amino, alkyl, or aminoalkyl.

24. The method of claim 19 wherein L is selected from misonidazole (MISO), metronidazole (METRO), 4-nitroimadazole (NI), and 2-amino-5-nitrothiazole (ANT).

25. The method of claim 16 or 19 wherein R is H.
26. The method of claim 38 wherein R is H.
27. The method of claim 16 or 19 wherein X is Cl.
28. The method of claim 24 wherein X is Cl.
29. The method of claim 28 wherein the compound of formula 1 is selected from mono-MISO, mono-METRO, mono-NI and mono-ANT.
30. The method of claim 2 or 5 wherein the compound of formula 1 is the trans isomer.

* * * * *